United States Patent [19]

Chang

[11] Patent Number: 4,711,844

[45] Date of Patent: Dec. 8, 1987

[54] MODIFIED SIGNAL PEPTIDES

[75] Inventor: Shing Chang, Hercules, Calif.

[73] Assignee: Cetus Corporation, Emeryville, Calif.

[21] Appl. No.: 473,820

[22] Filed: Mar. 9, 1983

[51] Int. Cl.$^4$ .................... C12N 15/00; C12N 1/20; C12N 1/00; C12P 21/00

[52] U.S. Cl. ................................ 435/317.1; 435/253; 435/172.3; 435/68; 935/47; 935/48; 935/50; 935/51

[58] Field of Search ................. 435/68, 240, 253, 317, 435/172.1, 172.3; 536/25, 26, 27; 935/23, 27, 29, 47, 48, 51, 50, 72, 73, 74

[56] References Cited

U.S. PATENT DOCUMENTS

4,338,397 7/1982 Gilbert et al. .................... 435/68

FOREIGN PATENT DOCUMENTS

0121352 10/1984 European Pat. Off. ......... 435/172.3

OTHER PUBLICATIONS

Lai et al, *Proc. Natl. Acad. Sci.*, vol. 78(6), pp. 3506–3510, Jun. 1981, "*Bacillus licheniformis* Penicillinase Synthesized in *Escherichia coli* Contains Covalently Linked Fatty Acid and Glyceride".

Gray et al, *J. Bact.*, V. 145(1), Jan. 1981, pp. 422–428, "Molecular Cloning and Expression of *Bacillus licheniformis* β-lactamase Gene in *Escherichia coli* and *Bacillus subtilis*".

Zoller et al, *Nucleic Acid Res.*, vol. 10, 1982, pp. 6887–6900, "Organonucleonase–Directed Mutagenesis Using M13–derived Vectorian Efficient and General Procedure for the Production of Point Mutations in any fragments of DNA.

Zweibel et al, *J. Bact.* V. 145(1), Jan. 1981, pp. 654–656, "Preferential Selection of Deletion Mutants of the Outer Membrane Lipoprotein Gene of *Escherichia coli* by Globomycin".

Vlasuk et al, *J. Biol. Chem.*, vol. 258(11), pp. 7141–7148, Jun. 1983, "Effects of the Complete Removal of Basic Amino Acid Residues from the Sound Peptide on Secretion of Lipoprotein in *Escherichia coli*".

Mezés et al, *J. Biol. Chem.*, vol. 258(18), Sep. 28, 1983, pp. 11211–11218, "Construction of a penPΔ1 *Bacillus licheniformis* 7441C β-Lactamase Lacking Site for Lipoprotein Modification".

Lin et al, *J. Bact.*, Feb. 1980, pp. 550–557, vol. 151(2), "Assembly of Outer Membrane Lipoprotein in an *Escherichia coli* Mutants with a Single Amino Acid Replacement within the Signal Sequence of Prolipoprotein".

Neugebauer et al, *Nucl. Acid Res.*, vol. 9(11), 1981, pp. 2577–2588, "Penicillinase from *Bacillus licheniformis*: Nucleotide Sequence of the Gene and Implications for the Biosynthesis of a Secretory Protein in a Gram–Positive Bacterium".

Nielsen et al, *J. Biol. Chem.*, vol. 257(8), Apr. 25, 1982, pp. 4490–4495, "Membrane–Bound Penicillinases in Gram–Positive Bacteria".

Inouye et al., *The EMBO Journal*, vol. 2, No. 1, pp. 87–91, 1983.

*Primary Examiner*—Thomas G. Wiseman
*Assistant Examiner*—Robin Lyn Teskin
*Attorney, Agent, or Firm*—Elliott L. Fineman; Virginia Meyer

[57] ABSTRACT

The invention discloses a method for producing modified signal peptides sequences derived from wild-type signal peptide sequences of the type that are capable of forming membrane-bound lipoproteins. Modified signal peptide sequences produced by the method of the invention are useful for increasing the secretion of heterologous gene products produced by transformed host organisms. The invention further discloses a method for producing recombinant DNA sequences in vivo.

6 Claims, 8 Drawing Figures

FIG. 1
GENERAL OVERVIEW

*Modified signal sequence
▲ "Heteroduplex recombination" method used.

FIG. 2

PROCESSING OF PRE-PENICILLINASE

```
            10                  20                  30                  40      45
             |                   |                   |                   |       |
(1)  M K L W F S T L K L K K A A A V L L F S C V A L A G C A N N Q T N A S Q P A E K N E K T E
                                                 ‾ ‾ ‾ ‾
                                                     *

(2)  C A N N Q T N A S Q P A E K N E K T E
                                           ‾

(3)  S Q P A E K N E K T E
```

| | | |
|---|---|---|
| M-Met | K-Lys | L-Leu |
| W-Trp | F-Phe | S-Ser |
| T-Thr | A-Ala | V-Val |
| C-Cys | G-Gly | N-Asn |
| Q-Gln | P-Pro | E-Glu |

FIG. 3

FIG. 4 pOG2254:
EcoRI (ClaI/HpaII)
GAATTC ...ATCGG....promoter....S/D.....ATG...GGA TGC GCT AAC AAT CAA ACG AAT GCC TCG...CTC GGG
                                          met.... gly cys ala asn asn gln thr asn ala ser.... leu gly
                                          1       26  27  28  29  30  31  32  33  34  35       61  62
                                                                                    AvaI pDH5452:
EcoRI                                              (ClaI) HindIII
GAATTC ----                                32  33  34  35
                                           ACG AAT GCC TCG ATA AGCTT tet
                                                         TaqI pDH5501:
EcoRI                                              (HindIII)
GAATTC ----                                32  33  34  35
                                           ACG AAT GCC TCG AGCTT tet
                                                         XhoI/TaqI pDH5508:
EcoRI                                      NaeI/HpaII
GAATTC ----                                32  33  34
                                           ACG AAT GCC GGC ---- : pBR322 DERIVED SEQUENCE (NOT COMPLETELY SHOWN)

——— : penP DERIVED SEQUENCE

S/D: SHINE–DALGARNO SEQUENCE

MODIFIED SIGNAL PEPTIDES

This invention relates to molecular biology and, more particularly to the art of recombinant DNA. Specifically, the invention relates to methods for producing modified signal peptides and to modified signal peptides useful for increasing the secretion of heterologous gene products produced by transformed hosts. The invention further relates to a method for producing recombinant DNA sequences in vivo.

Although protein synthesis occurs intracellularly, some proteins function outside the cell. These extra-cellular proteins are referred to as secreted proteins. Many of the secreted proteins are expressed initially inside the cell in a precursor or a pre-protein form. These pre-proteins contain an appended amino terminal extension called a signal or leader sequence (or signal peptide). The signal sequence plays an essential role in transporting the appended peptide into and/or through limiting cellular membranes.

These signal sequences are especially useful in the creation of cloning vectors. The use of such vecotrs now makes it possible to transform compatible host organisms to they will produce heterologous gene products. The host organisms are often bacteria since bacteria can be grown with relative ease in chemically defined media. Growth of the organisms is rapid and high product yields are possible. When suitable host bacteria are transformed to produce desired gene products, such gene products are often easier to detect and purify if they are secreted into the periplasmic space or into the growth medium. Secretion of desired gene products into the medium avoids the necessity of breaking up the host organisms in order to recover the product. In addition, some heterologous gene products have a toxic affect on the host organisms. When such heterologous gene products are secreted rather than being allowed to accumulate within the host, they are less likely to interfere with normal cellular functions.

In some instances, the signal sequence is cleaved proteolytically during or after secretion to yield a mature protein product that is dissociated from the limiting cellular membranes through which it passed. In other instances, although the signal sequence is also cleaved, the mature protein remains bound to the cell membrane because of further modifications which lead to covalent attachments of lipid to the amino termini of the mature protein. *Escherichia coli* lipoproteins are an example of such membrane-bound proteins. *Escherichia coli* beta-lactamase is an example of a protein that is dissociated from membrane following cleavage of the signal sequence. As a result the mature beta-lactamase is secreted into the *Escherichia coli* periplasmic space. Such secreted proteins are called exoproteins. Other proteins, however, such as *Bacillus licheniformis* beta-lacatamase, which herein is also referred to as penicillinase, can be processed into two different protein forms, one of which is a secreted exoprotein form, the other of which is a membrane-bound lipoprotein form. In penicillinase, the 34 amino terminal amino acids constitute the signal peptide for the exopenicillinase form. In the lipoprotein form of penicillinase, the first 26 of these 34 amino acids appear to function as the actual transport portion of the signal peptide. Some or all of the remaining 8 amino acids appear to be involved, along with some of the carboxy-terminal amino acids in the transport portion of the signal peptide, in the formation of the lipoprotein form.

Although not entirely understood, the mechanism by which mature protein becomes bound to a cell membrane appears to involve the formation of a lipid bond at a site located near the signal peptide. Attachment of the lipid appears to anchor the protein into the cellular membrane. Specific amino acid sequences in the junction region of the signal sequences and the mature protein capable of forming membrane-bound forms are believed to function as recognition sites for the cellular agents involved in the chemical modifications leading to the formation of the membrane-bound lipoproteins. These specific chemical modifications are thought to include covalent bonding of fatty acids to the signal sequence moieties.

The usefulness of signal sequences capable of promoting lipoprotein formation would in some cases be improved if the recognition sequences could be modified in a way that would increase the amount of unbound exoprotein that is secreted into the periplasmic space or into the growth medium. Such a modified signal sequence would of course also lead to a decrease in the amount of the membrane-bound lipoprotein that is formed.

It is an object of the present invention to provide a method for producing modified signal peptide useful for increasing the secretion of heterologous gene products produced by transformed bacterial hosts.

It is a further object of the present invention to provide a method for producing modified bacterial signal peptide sequences that can be used to increase the secretion of heterologous gene products produced by transformed bacterial hosts.

A still further object of the present invention is to provide a method for producing modified *Bacillus licheniformis* penicillinase signal peptide sequences that can be used to increase the secretion of heterologous gene products produced by transformed bacterial hosts.

It is an object of the present invention to provide modified signal peptide sequences useful for increasin9 the secretion of heterologous gene products produced by transformed bacterial hosts.

It is a further object of the present invention to provide modified bacterial signal peptide sequences that can be used to increase the secretion of heterologous gene products produced by transformed bacterial hosts.

A still further object of the present invention is to provide modified *Bacillus licheniformis* penicillinase signal peptide sequences that can be used to increase the secretion of heterologous gene products produced by transformed bacterial hosts.

Another object of the present invention is to provide a method for producing recombinant DNA sequences in vivo.

Other objects of the invention will become apparent to those skilled in the art from the following description, taken in connection with the accompanying drawings wherein:

As used herein, the terms signal peptide, leader peptide, signal sequence and leader sequence are used interchangeably. Such terms are meant to denote amino terminal protein extensions responsible for transport of the protein into or through cell membrane. For proteins that can be processed as membrane-bound lipoproteins, the terms signal peptide and signal sequence are meant to include specific amino acid sequences in the junction region of the signal sequences and the mature protein that are believed to function as recognition sites for the cellular agents involved in chemical modifications leading to the formation of the membrane-bound lipoprotein forms.

As used herein, the letters A, T, C, G are meant to denote the nucleotides adenine, thymine, cytosine, and guanine in DNA respectively. The letter N is used to mean any deoxyribonucleotide, i.e. A or T or C or G.

As used herein, the term p is meant to denote the prepenicillinase gene encoded by Bacillus licheniformis strain 749/C. The nucleotide sequence of penP has been published by Kroyer, J., and Chang, S., Gene 15:343–347 (1981), and Neugebauer, K., Sprengel, R., and Schaller, H., Nucleic Acids Research 9:2577–2589 (1981).

As used herein, the term fused peptide or fused protein is meant to denote an amino acid sequence comprised of a signal sequence or a portion thereof joined to a series of heterologous amino acids, the sequence of which is determined by a segment of heterologous DNA. Fused peptide and fused protein are used interchangeably. As used herein, the term appended peptide is meant to denote the series of heterologous amino acids fused to the signal peptide or a portion thereof.

As used herein, conserved sequence is meant to denote a leucine-alanine-glycine-cysteine (Leu-Ala-Gly-Cys) amino acid sequence, or a conserved sequence of amino acids "comparable" to the Leu-Ala-Gly-Cys sequence, found at the end or junction region of the signal peptides of some lipoproteins, and in prepenicillinase from several gram positive organisms. A "comparable" conserved sequence will contain a cysteine moiety and will also contain amino acids in the junction region between the signal peptide and its appended peptide that are capable of creating a hydrophilic area to surround the cysteine moiety. See generally Nielsen, J. B. K., and Lampen, J. O., Journal of Biological Chemistry, 257:4490–4495 (1982).

As used herein, the term membrane binding is meant to denote the anchoring on or anchoring into membrane of fused proteins by means of modifications of amino acids comprising the amino terminal portion of said fused proteins.

As used herein, the letters hGH are meant to denote human growth hormone.

As used herein, substantial structural homology means DNA molecules having sufficient sequence duplication to allow their complementary strands to anneal with one another and recircularize to form heteroduplexes.

As used herein, substantial sequence homology is meant to denote nucleotide sequences that are substantially functionally equivalent to one another. Nucleotide differences between such sequences having substantial sequence homology will be de minimus in affecting the function of the gene products coded for by such sequences.

As used herein, a transformable host means a host organism capable of accepting plasmid DNA. Transformable hosts are thus capable of being transformed by plasmid DNA.

As used herein, progeny plasmids are meant to denote offspring or daughter cells produced during cell division where the offspring or daughter cells are substantially functionally equivalent to the parental cell.

As used herein, derivative plasmids are meant to denote offspring produced during recombination. Derivative plasmids resulting from such recombinations will not be functionally equivalent to the parental cells.

As used herein, amino acid abbreviations are:

| Phelylalanine | Phe | Histidine | His |
| Leucine | Leu | Glutamine | Gln |
| Isoleucine | Ile | Asparagine | Asn |
| Methionine | Met | Lysine | Lys |
| Valine | Val | Aspartic acid | Asp |
| Serine | Ser | Glutamic acid | Glu |
| Proline | Pro | Cysteine | Cys |
| Threonine | Thr | Tryptophan | Try |
| Alanine | Ala | Arginine | Arg |
| Tyrosine | Tyr | Glycine | Gly |

The methods of the present invention make use of techniques of genetic engineering and molecular cloning As used herein, genetic engineering means techniques which lead to the formation of new combinations of heritable material by the insertion of nucleic acid molecules, produced or derived by whatever means outside the cell, into a bacterial plasmid or other vector system so as to allow their incorporation into a host organism in which they do not naturally occur at high frequency but in which they are capable of replication. General techniques of genetic engineering and molecular cloning are included in Maniatis, T., Fritsch, E. F., and Sambrook, J., Molecular Cloning: A Laboratory Manual, Cold Spring Harbor Laboratory (1982), and Methods in Enzymology, Volume 68, Recombinant DNA, (Wu, R., editor), Academic Press, New York, 1979.

Very generally, the invention discloses a method for producing modified signal peptide sequences derived from wild-type signal peptide sequences of the type that are capable of forming membrane-bound lipoproteins. As used herein, derived from is meant to include mutated or synthetic signal sequences having substantial sequence homology with wild-type signal sequences. The wild-type sequences includes a conserved recognition region near the carboxyo-terminal end or junction region of the signal peptide sequences. This conserved region has a single cysteine moiety, the presence of the cysteine being necessary for the formation of the membrane-bound lipoprotein. In the method of the invention, the deoxyribonucleotide codon coding for the cysteine is replaced with a deoxyribonucleotide codon coding for an amino acid other than cysteine that will not function to form membrane-bound lipoprotein. The invention also discloses modified signal peptide sequences that are modified in accordance with the method of the invention.

The invention further discloses a method for producing recombinant DNA sequences wherein two parental plasmids having substantial structural homology, except for a portion thereof, are converted from closed circular forms to open blunt-ended linear forms. The blunt-ended double-stranded linear DNA is separated and allowed to anneal and recircularize randomly to form heteroduplexes having single-stranded DNA sequence portions corresponding to the different DNA sequence portions on the two parental plasmids, respectively. These heteroduplexes are then introduced into transformable hosts and the transformable hosts are allowed to accomplish n vivo recombination of the single-stranded DNA sequence portions of the recircularized heteroduplexes, thereby producing derivative plasmids containing recombinations of the different DNA sequence portions carried on the two parental plasmids. The recombined plasmids are then screened for the derivative plasmids carrying desired recombinations which are used to transform competent and susceptible host organisms.

More specifically, the invention discloses a method for producing modified signal peptide sequences derived from or having substantial sequence homology with wild-type sequences capable of forming membrane-bound lipoproteins. *Bacillus licheniformis* penicillinase signal peptide sequences, *Escherichia coli* lipoprotein (lpp gene product) signal peptide sequences and *Bacillus cereus* penicillinase signal sequences are examples of wild-type sequences capable of forming membrane-bound lipoproteins. *Bacillus licheniformis* penicillinase signal peptide sequences are especially preferred in practicing the method of the invention for producing the modified signal peptide sequences. The wild-type signal peptide sequences capable of forming membrane bound lipoproteins useful in the method of the present invention include "conserved" regions or sequences comprised of the amino acids Leu-Ala-Gly-Cys, or amino acids that are comparable to them. In the *Bacillus licheniformis* penicillinase (penP) signal peptide, the conserved Leu-Ala-Gly-Cys region is located at amino acid positions 24-27. The conserved sequence around the cysteine residue allows the cysteine to participate in the formation of the covalent bonds that will bind fatty acids to the peptide moiety. A conserved tetra-amino acid sequence comprised of Leu-Ala-Gly-Cys is found in several of the signal peptides capable of forming membrane bound lipoproteins. Specific examples include the signal peptides from *Bacillus licheniformis* penicillinase, *Escherichia coli* lipoproteins (pp gene product), and *Bacillus cereus* penicillinase. See generally, Nielsen, J. B. K., and Lampen, J. O., *Journal of Biological Chemistry*, 257:4490–4495 (1982).

The method of the invention for producing modified signal peptide sequences comprises substituting the DNA nucleotide condon coding for the cysteine in the conserved amino acid sequence with a DNA nucleotide codon coding for an amino acid other than cysteine, said other amino acid being one that will not function to form membrane-bound lipoprotein. Especially preferred is substituting the codon coding for the amino acid cysteine with a codon coding for the amino acid serine. DNA nucleotide substitution can be accomplished using methods known to those skilled in the art. Such methods include the method for single nucleotide alteration disclosed in U.S. Pat. No. 4,351,901, issued to Chander P. Bahl, Sept. 28, 1982. A more preferred method for accomplishing the nucleotide substitution is the method of primer directed mutagenisis. See Zoller, M. J., and Smith, M., *Nucleic Acids Research*, 10:6487–6500 (1982). In utilizing the more preferred primer directed mutagenisis method, the DNA sequence of the signal peptide sequence surrounding the cysteine to be substituted is determined. Once the DNA sequence surrounding the codons coding for the cysteine to be substituted is determined, a synthetic nucleotide primer fragment of approximately 15 nucleotides is synthesized using methods known to those skilled in the art. Such methods include the diester method of Narang, S. A., Hsiung, H. M., and Brousseau, R., in *Methods in Enzymology*, 68:90–98, (Wu, R., editor), Academic Press (1979).

The synthetic nucleotide fragment will complement the anti-sense strand of the signal sequence in the area of the cysteine to be substituted. More specifically, when the preferred penP signal sequence is being utilized as the signal sequence to be modified, the synthetic fragment will correspond to the codons for the 5 amino acids from positions 25 to 29, except that the middle nucleotide in the synthetic primer will have a mismatched nucleotide that does not complement the corresponding nucleotide in the penP template. When wild type signal sequences other than penP are used, the synthetic primer will contain mismatched nucleotides that will not complement the wild-type nucleotides in the region of the cysteine codon to be modified in those signal sequences.

The wild-type penP signal sequence contains the codon (TGC), which codes for the cysteine at amino acid position 27. When the modified penP signal sequence contains a serine at amino acid position 27, the synthetic fragment will contain a TCC sequence in this position and thus code for serine and not cysteine. In practicing the method of the invention, the wild-type signal sequence to be modified is isolated from an organism or plasmid containing it. The wild-type penP signal sequence can be isolated from a plasmid such as pOG2165 (ATCC 31777) using appropriate restriction enzymes. Plasmid pOG2165 is described in European Patent Application Publication No. 0,036,259. Following purification of the DNA sequence containing the wild-type signal sequence, the fragment is ligated to the replicative form (RF) of a single-stranded DNA phage such as coliphage M13mp9. See Viera, J., and Messing, J., Gene, 19:259–268 (1982), and Messing, J. and Viera, J., Gene, 19:269–276 (1982). A recombinant coliphage carrying the wild-type signal sequence is isolated and identified. The synthetic nucleotide fragment carrying the mismatched nucleotide is first annealed to the template phage DNA carrying the wild-type penP leader sequence. The synthetic fragment is then used as a primer to initiate the synthesis of the complementary strand DNA in vitro. In constructing the specific cysteine to serine mutation, complementary (minus) strands are synthesized by primer extension reaction using Klenow fragment of *Escherichia coli* DNA polymerase I on the phage DNA template. In the presence of T4 DNA ligase in this reaction, a fraction of the DNA molecules are converted to double-stranded, covalently-closed relaxed circles. These molecules are separated from the other molecules which either were incompletely extended by polymerase or failed to be ligated due to the incomplete kinase reaction of the primer. The molecules are separated by agarose gel electrophoresis. Purified covalently closed double-stranded DNA is then used to transfect competent *Escherichia coli* cells. Transformants containing phages carrying the modified signal sequences are identified and isolated. The modified signal fragment containing the cysteine to serine mutation is removed from the recombinant phage. Following purification, it is cloned into a suitable cloning vector in place of the corresponding wild type signal sequence that had previously been cloned into this plasmid.

Modified signal peptides produced according to the method of the invention will contain an amino acid X, i.e., an amino acid other than cysteine, in place of the cysteine contained within a conserved region located near the carboxy-terminal end or junction region of the signal peptide sequences. Especially preferred is a modified *Bacillus licheniformis* penicillinase (penP) signal sequence containing a serine at amino acid position 27 of the signal peptide sequence. The serine at amino acid position 27 replaces the cysteine found within the conserved Leu-Ala-Gly-Cys extending from amino acid positions 24-27 in the wild type *Bacillus licheniformis* penP signal sequence. Also preferred is a modified penP signal sequence containing an alanine at amino acid position 27 to replace the cysteine found at this location in the wild-type *Bacillus licheniformis* penP signal sequence.

More specifically, the invention also discloses a method for producing recombinant DNA sequences in vivo. In practicing this aspect of the invention, a pair of parental plasmids is utilized. The parental plasmids will have substantial structural homology with one another but each will contain a segment of DNA coding for a desired gene product that will not be found on the other parental plasmid. For example, parental plasmid (A) might contain a gene which will code for a desired gene product (a). Parental plasmid (A') will have substantial sequence homology with parental plasmid (A) but will contain a structural gene (b) coding for a second desired gene product. The pair of parental plasmids, (A) and (A'), are each linearized with a restriction enzyme. If the restriction enzyme digestion leaves single-stranded tails, the termini are made blunt with a single-strand specific nuclease such as S1. Duplexed molecules are then formed by melting and annealing. Molecules referred to as homoduplex molecules will contain DNA strands only from parental plasmid (A) or from parental plasmid (A'). Heteroduplex molecules will contain a DNA strand from parental plasmid (A) as well as a DNA strand from parental plasmid (A'). Homoduplex molecules do not transform hosts efficiently due to their inability to circularize. Because heteroduplex molecules will contain DNA strands from both parental plasmids, they will be able to recircularize. In their circularized form they are able to transform hosts efficiently. Unique sequences, such as (a) and (b), on each of the parental strands (the mismatched sequences) in the heteroduplexes can be selectively incorporated into or deleted from derivative plasmids as a result of the in vivo repair activities in transformed cells. In addition, mispaired sequences due to allelic differences between the parental plasmids can be incorporated into the derivative plasmids as well. This method of the present invention permits the generation of new recombinant sequences in plasmids in vivo without relying solely on the direct ligation of restriction fragments in vitro. In a preferred form of this aspect of the invention, parental plasmids are selected which contain sufficient sequence homology to allow single strands of DNA from each plasmid to anneal with single strands of DNA from the other plasmid. The parental plasmids will each contain unique sequences that will not be found on the other parental plasmid. The parental plasmids DNA will be isolated using techniques known to those skilled in the art. Such techniques include cesium chloride gradients and the small scale method of Ish-Horowicz, D., and Burke, J. R., *Nucleic Acids Research* 9:2989-2998 (1981). Each parental plasmid is cleaved with an appropriate restriction enzyme. Use of such enzymes is well known to those skilled in the art. Such enzymes can be purchased from sources such as New England Biolabs or Bethesda Research Laboratories and used according to suppliers specifications.

Figure 7:
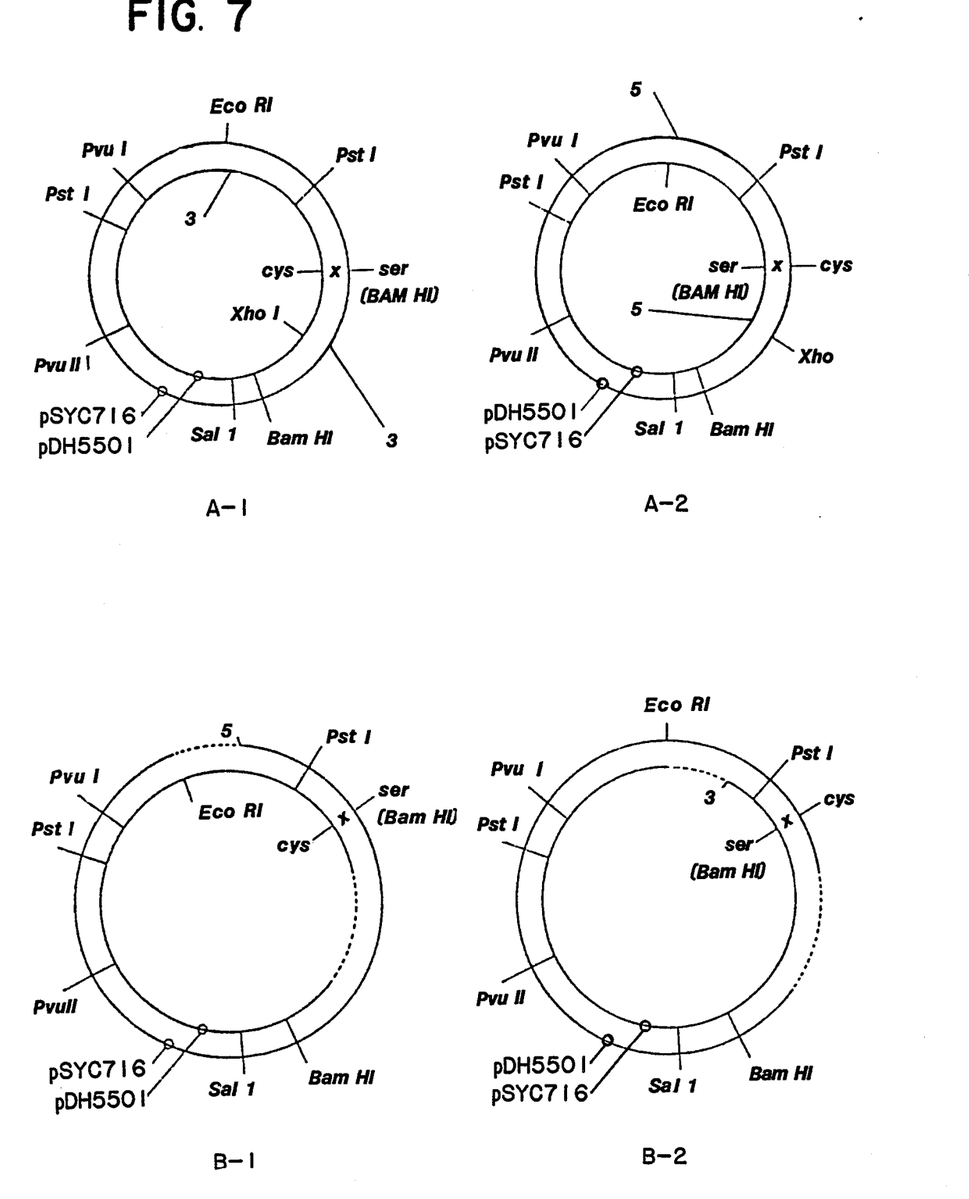
FIG. 7 is a diagram illustrating the structure of heteroduplexes formed from parental plasmids pSYC716 and pDH5501.

To prepare the heteroduplexes, linearized plasmid DNA, if it contains single-stranded protruding ends, is first treated with an enzyme such as S1 nuclease in an appropriate buffer in order to digest the single-stranded tails that can result from restriction enzyme digestion. Following treatment with the S1 nuclease, the plasmid DNA is extracted and precipitated. The plasmid DNA is then resuspended in an appropriate annealing buffer. A solution containing both parental DNA's is heated for an amount of time sufficient to separate the strands of DNA. The heated solution is then allowed to gradually cool at room temperature to permit the separated DNA single strands to anneal with one another and circularize. The heteroduplex circularized DNA is separated from the homoduplex double strands that did not circularize. The heteroduplex DNA is then used to transform a transformable host. The hanging tails and single-stranded gaps in the heteroduplex molecules, as illustrated in FIG. 7, will be removed or repaired by transformed cells n vivo. This in vivo recombination will result in the formation of new recombinant derivative plasmids. Mispaired sequences due to allelic differences between the parental plasmids can also be incorporated with high frequency into the recombinant derivative plasmids by means of the heteroduplex transformation procedure of the present invention. Clones carrying the desired recombinant derivative plasmids are isolated. The recombinant derivative plasmids are isolated and used to transform transformable hosts.

Specific embodiments of the present invention are outlined in the following examples. Such examples are for illustrative purposes only and are not intended to limit the scope of the claims in any way.

EXAMPLE I

Construction of a deletion mutation at amino acid positions 24 through 28 in *Bacillis licheniformis* penicillinase The DNA sequence of the *Bacillis licheniformis* penicillinase (penP) gene is known. See Kroyer, J., and Chang, S., *Gene* 15:343-347 (1981) and Neugebauer, K., Sprengel, R., and Schaller, H., *Nucleic Acids Research* 9:2577-2589)1981). The DNA nucleotide sequencing data reveals that there are only two HhaI (GCGC) recognition sequences in the penP gene clustered at the coding sequences for the 23rd to 28th amino acids. These two HhaI sites in the penP gene flank the conserved Leu-Ala-Gly-Cys sequence. This same conserved Leu-Ala-Gly-Cys sequence is found in the signal peptides of several lipoproteins.

Without knowing whether cells expressing a mutated penP gene containing the deletion covering this sequence would be viable, it was decided to initially generate the deletion mutation in a promoterless penP gene. This was made possible by using a plasmid designated plasmid pSYC423 which replicates in both *Escherichia coli* and *Bacillus subtilis* cells. Plasmid pSYC423 carries the complete coding sequence of *Bacillus licheniformis* penP, but lacks of its promotor. The penP sequence on plasmid pSYC423 is carried on a fragment flanked by EcoRI and BamHI sites. This plasmid, pSYC423, which contains many other HhaI sites outside of the EcoRI and BamHI was first digested with HhaI enzymes, and the 3' protruding termini were then made blunt using the Klenow fragment from *Escherichia coli* DNA polymerase HhaI in the presence of four deoxyribonucleotide triphosphates. Such methods are well known to those skilled in the art and can be found in such references as Maniatis, T., Fritsch, E. F., and Sambrook, J., *Molecular Cloning: A Laboratory Manual,* Cold Spring Harbor Laboratory, 1982. The blunt-ended HhaI fragments from plasmid pSYC423 were further digested with EcoRI and BamHI enzymes. Such enzymes were obtained from New England Biolabs and were used according to the manufacturers instructions. The EcoRI-HhaI fragment containing the 5' portion (337 nucleotides) of gene was purified by elution from acrylamide gels. The HhaI-BamHI fragment (lkb) was purified from agarose gel. In a separate experiment, the large EcoRI to BamHI fragment on pSYC423 was also purified and ligated to these two penP derived fragments. The plamsid that resulted designated plasmid pSYC562, contains a deletion covering the coding sequence for the Leu-Ala-Gly-Cys-Ala (positions 24-2 on the wild-type *Bacillus licheniformis* penP gene). The remaining portion of pSYC562 is the same as that on plasmid pSYC423. Taking advantage of a nearby PstI site located 27 nucleotides upstream from the deletion, plasmid pSYC562 was digested with PstI, end-labeled and then its sequence was analyzed. See Gilber, W., and Maxam, A., in *Methods in Enzymology* 65:499–560 (Grossman, L., and Moldave, K. J., editors) Academic Press (1980). The results confirmed that the sequence contained a deletion of nucleotides coding for amino acid residues from positions 24 through 28. This mutation is termed penP delta 2428.

In order to study the phenotype of the delta 2428 mutation, a wild-type penP promoter was added back to plasmid pSYC562. The 313 base pair (bp) EcoRI to PstI fragment containing the promoter and partial coding sequence preceding the delta 2428 mutation of penP was purified from plasmid pSYC310-2 (the parent of pSYC423). Plasmid pSYC310-2 is described by McLaughlin, J. R., Chang, S-Y., and Chang, S., *Nucleic Acids Research* 10:3905–3919 (1982). The fragment was then ligated with EcoRI- and PstI- digested DNA of plasmid pSYC562 in place of the small EcoRI to PstI fragment. *Escherichia coli* transformants resistant to ampicillin were selected and a representative plasmid, pSYC617, was studied further. Based on analysis of fragmentation patterns using various endonucleases, plasmid pSYC617 was found to be identical to plasmid pSYC310-2 except for the presence of the 15 base pair deletion in penP delta 2428 as expected from the fragment switching experiment.

When plasmid pSYC617 was used to transform competent cells of *Escherichia coli* CS412 the majority of the mature penicillinase remained bound to membrane. Only very low levels of exopenicillinase were detected. Thus it was concluded that deletion of the conserved sequence containing the cysteine at amino acid position 27 of the *Bacillus licheniformis* signal sequence interferes with the production of exoenzyme.

EXAMPLE II

Construction of a cysteine to serine mutation at amino acid position number 27 in the *Bacillus licheniformis* pnicillinase signal sequence

Figure 2:
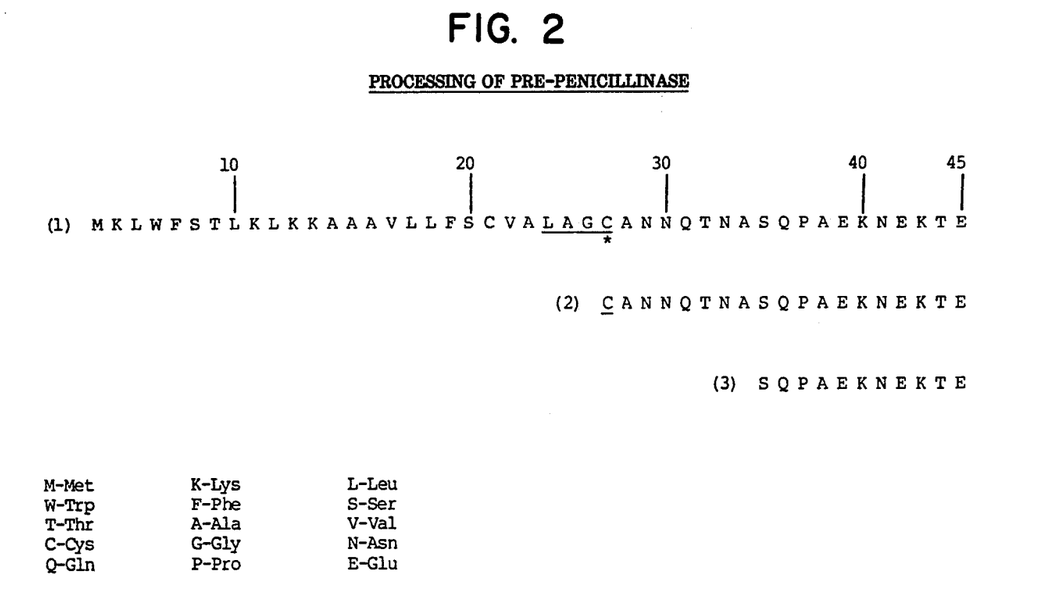
FIG. 2 is an amino acid sequence diagram illustrating the processing of prepenicillinase.

*Bacillus licheniformis* penicillinase (penP) gene has been sequenced. See Kroyer, J., and Chang, S., Gene 15:343–347 (1981) and Neugebauer, K., Sprengel, R., and Schaller, H., *Nucleic Acids Research* 9:2577–2589 (1981). The signal sequence contains the codon TGC which codes for a cysteine at amino acid position 27. Good evidence exists which suggests that the cysteine residue at position 27 is modified as part of a sequence of events leading to formation of the membrane-bound form of penicillinase. See Nielsen, J. B. K., Caulfield, M. P., and Lampen, J. O., *Proceedings National Academy Science,* (USA) 78:3511–3515 (1981), and Lai, J. S., Sarvas, M., Brammar, W. J., Neugebauer, K., and Wu, H. C., *Proceedings National Academy Science,* (USA) 78:3506–3510 (1981). Also see FIG. 2. To specifically alter this biosynthetic pathway, it is necessary to mutate the sequence in the penicillinase signal sequence gene coding for cysteine at this position.

Because of its simplicity and efficiency, the method of primer-directed mutagenesis (see Zoller, M. J., and Smith, M., *Nucleic Acids Rsearch* 10:6487–6500 (1982) was used for the construction of the cysteine to serine mutation. A DNA fragment containing wild-type penicillinase or penP gene sequence was isolated. Specifically the DNA fragment located between the HindIII and BamHI sites was excised from plasmid PSYC310-2 . See McLaughlin, J. R., Chang, S. -Y., and Chang, S., *Nucleic Acids Research* 10:3905-3919 (1982). Plasmid pSYC310-2 is a bifunctional plasmid capable of replicating in both *Bacillus subtilis* and *Escherichia coli.* It carries the wild-type penP gene from *Bacillus licheniformis.* Those skilled in the art will realize that the wild-type penP gene could have been excised from other engineered recombinant plasmids that carry it. One such plasmid is *Bacillus subtilis* plasmid pOG2165 (ATCC 31777). The excised HindIII-BamHI DNA fragment from pSYC310-2 was purified by gel elution and then ligated to Replicative Form (RF) DNA of coliphage M13. See Viera, J., and Messing, J., Gene 19:259–268 (1982) and Messing, J., and Viera, J., *Gene* 19:269–276 (1982).

Specifically the purified HindIII-Bam-HI fragment from pSYC310-2 was ligated to M13mp9, obtained from Bethesda Research Laboratories, Inc., P.P. Box 577, Gaithersburg, Md., that had previously been digested with restriction endonucleases HindIII and BamHI. A recombinant phage carrying the penP gene, i.e. recombinant phage M13-CMl, was identified and single-stranded phage DNA was prepared from this clone. The methods used are described in Zoller, M. J., and Smith, M., *Nucleic Acids Research* 10:6487–6500 (1982).

Figure 3:
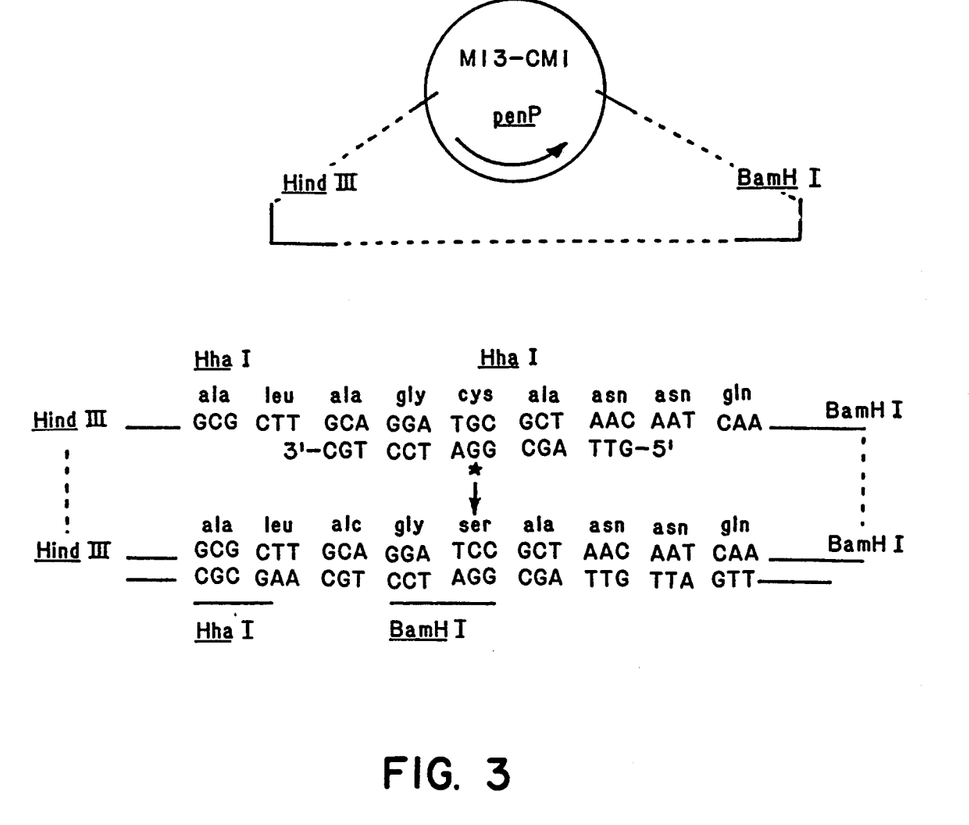
FIG. 3 is a codon diagram illustrating the construction of the cysteine$_{27}$ to serine$_{27}$ mutation.

The basic approach for this method is illustrated in FIG. 3. A 15-nucleotide synthetic fragment 5'-GTTAGCGGATCCTGC-3', made by the diester method of Narang, S. A., Hsiung, H. M., and Brousseau, R., in *Methods in Enzymology* 68:90–97 (R. Wu, editor) Academic Press (1979), was employed as a primer to initiate the synthesis of the complementary strand in vitro after the primer has been annealed to the template M13-CMl DNA. This primer complements the anti-sense strand of the penP sinal sequence gene segment corresponding to the codons for the five amino acids from positions 25 to 29, except that the middle nucleotide in the synthetic primer is a mismatched nucleotide that does not complement the corresponding nucleotide in the wild-type penP gene template. Incorporation of the mismatched sequence into the penP gene causes conversion of the cysteine (TGC codon) to serine (TCC codon) at position 27. See FIG. 3.

The alteration on the encoded peptide is essentially a conversion of the —SH group on the cysteine$_{27}$ to the —OH group of the serine$_{27}$. At the nucleotide level, a mutant gains a BamHI site (GGATCC) and loses the I (GCGC) at the mutation locus. See FIG. 3 for the change of the original GGATCGC sequence to GGATCCGC. The presence of a new BamHI site was the phenotype used to identify the mutants carrying the specific "G to C" nucleotide mutation.

In constructing the cysteine to serine mutation, complementary (minus) strands were synthesized by primer-extension reaction using Klenow fragment of *Escherichia coli* DNA polymerase I on the M13-CMl phage DNA template. Zoller, M. J., and Smith, M., *Nucleic Acids Research* 10:6487–6500 (1982). In the presence of T4-DNA ligase in this reaction, a fraction of the DNA molecules was converted to double-stranded, covalently-closed relaxed circles. These molecules were separated from other molecules, which either were incompletely extended by polymerase or failed to be ligated due to the incomplete kinase reaction of the primer. Separation was accomplished by agarose gel electrophoresis. This was carried out by applying the reaction mixture on a 0.8% agarose gel in the presence of 2 micrograms/ml of ethidium bromide. The band containing covalently closed circular DNA was excised and DNA recovered.

Purified covalently closed double-stranded DNA was used to transfect competent cells of *Escherichia coli* JM103 using standard transformation procedures for M13 phage. JM103 cells were obtained from Bethesda Research Laboratories, Inc., P.O, Box 577, Gaithersburg, Md. Also see generally, Viera, J., and Messing, M., *Gene* 19:259–268 (1982) and Messing, J., and Viera, J., *Gene* 19:269–276 (1982). A total of 36 phage plaques were isolated and RF DNAs from the phage-producing cells were analyzed using the quick plasmid screening method of Ish-Horowicz and Burke. See Ish-Horowicz, D. I., and Burke, J. F., *Nucleic Acids Research* 9:2989–2998 (1982). Upon digestion with BamHI restriction endonuclease, one of the 36 DNA preparations (designated M13-SYC458) yielded two fragments on agarose gel following electrophoresis, indicating that the "G to C" mutation had been incorporated into the gene sequence of that clone (M13-SYC458). The rest of the preparations showed a single cleavage by BamHI endonuclease indicating that the parental M13-CMl DNA had not been mutated at this locus. Further analyses of the DNA from the mutant, M13-SYC458, using HhaI and BamHI endonucleases, showed the expected sequence alterations. Direct sequence analysis of this mutation further confirmed the sequence change as shown in FIG. 3.

The cysteine to serine mutation in M13-SYC458 is located between the PsI and the BglII in the penP gene. McLaughlin, J. R., Chang, S.-Y., and Chang, S., *Nucleic Acids Research* 10:3905–3919 (1982) for the location of these sites. This restriction DNA fragment can be isolated from a mutant, prepared according to the primer directed mutagenesis method just described, that carries the cysteine to serine mutation. The "mutant" restriction fragment can then be cloned into a plasmid such as bifunctional plasmid pOG2165 (ATCC 31777) in place of the corresponding wild-type sequence.

Figure 1:
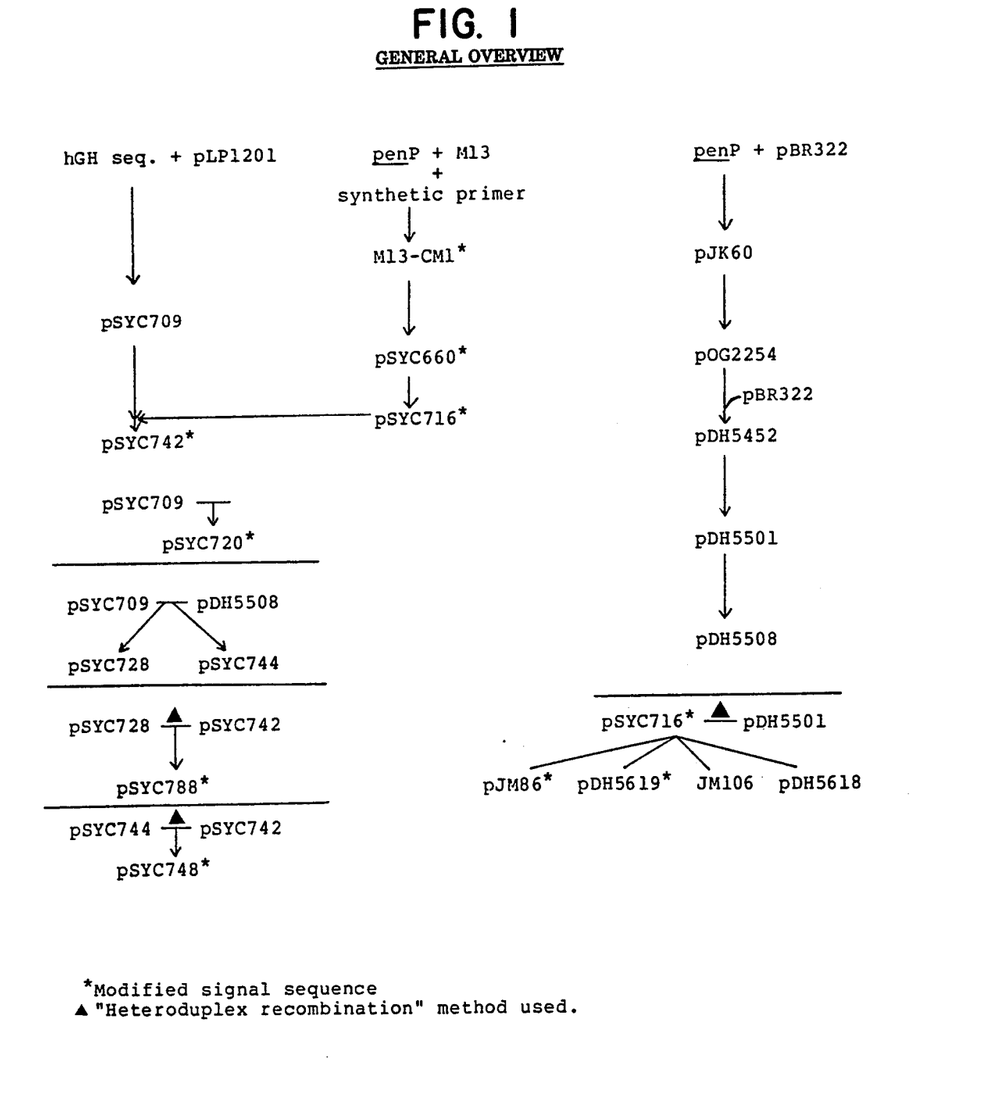
FIG. 1 is a general overview chart illustrating the derivation and construction of plasmids used to disclose the present invention.

When the "mutant" PstI or BgLII fragment was isolated and cloned into plasmid pSYC310-2, using standard techniques, in place of the corresponding wild-type sequences between these restriction sites, a plasmid designated as pSYC660 resulted. Plasmid pSYC660 is included in the general plasmid overview in FIG. 1.

Plasmid pSYC660 contains the cysteine to serine mutation at amino acid position 27 of the penP signal sequence. Heterologous DNA inserted behind the modified original sequence, will be expressed by transformed hosts as a peptide fused to the modified signal sequence. Such peptides are secreted more efficiently than those fused to wild-type signal sequences as shown in Example IX.

EXAMPLE III

Construction of a cysteine to alanine mutation at amino acid position number 27 in the *Bacillus licheniformis* penicillinase signal sequence Following the procedures outlined in Example II, it is possible to create a cysteine to alanine mutation at amino acid position 27. The wild-type penP sequence contains the codon TGC which codes for the cysteine at amino acid position 27. The serine$_{27}$ modified signal peptide coding sequence contains the codon TCC which codes for the serine at amino acid position 27. By converting the T of the TCC serine codon to a G, a GCC codon is created which codes for alanine.

The serine$_{27}$ modified penP signal sequence is located on M13-SYC458 phage. See Example II, supra. A synthetic primer is synthesized having the sequence 5'-GTTAGCGGAGCCTGC-3'. The primer is used to initiate the synthesis of the complementary strand in vitro after the primer is been annealed to the template M13-SYC458 DNA. This primer complements the anti-sense strand of the modified (ser$_{27}$) signal sequence gene segment corresponding to the codons for the five amino acids from positions 25 to 29, except that the middle nucleotide in the synthetic primer is a mismatched nucleotide that does not complement the corresponding nucleotide in the modified penP gene template. Incorporation of the mismatched sequence into the penP gene causes conversion of the serine (TCC codon) to alanine (GCC codon) at position 27. See FIG. 3.

EXAMPLE IV

Construction of a series of plasmids having convenient restriction sites flanking the *Bacillus licheniformis* penicillinase penP promoter and signal sequences.

The penicillinase penP gene from *Bacillus licheniformis* has been sequenced. The sequence data revealed a 446 base pair HpaII fragment (see Kroyer, J., and Chang, S., *Gene* 15:343–347 (1981) and Gray, O., and Chang, S., *Journal Bacteriology* 145:422–428 (1981)) comprising the penP promoter gene and the coding sequence for the first 72 amino acids. The penP signal peptide is included within this sequence of amino acids. The 446 base pair HpaII fragment was purified from plasmid pTB2 ( Kroyer, J., and Chang, S., Gene 15:343-347 (1981)) and then ligated with pBR322 (ATCC 37017) that had been digested with ClaI enzyme (both HpaII and ClaI enzymes give 5'-CG protruding ends). The ligated DNA was used to transform *Escherichia coli* competent cells prepared from strain CS412. Ampicillin-resistant transformants were selected. One of the transformants that was analyzed revealed the presence of the 446 base pair insert. This plasmid, designated pJK60, was used for further construction.

There is an VI site in the penP gene (CTCGGG, see Kroyer, J., and Chang, S., *Gene* 15:343-347 (1981)). There is also an AvaI site in pBR322 at position 1424 ( Sutcliffe, J. G., *Cold Spring Harbor Symposium Quantitative Biology* 43:77-90 (1979)). Plasmid pJK60 was digested with AvaI enzyme which cuts pJK60 in two locations; one originating from penP and the other originating from pBR322. This restricted DNA's from pJK60 was ligated and then used to transform *Escherichia coli* competent cells prepared from CS412. Chartacterization of plasmid DNA from one ampicillin-resistant transformant revealed that it has a unique AvaI site. This allowed a small AvaI fragment originally located on pJK60 to be delted; the resulting recombinant plasmid was designated pOG2254.

Plasmid pOG2254 contains sequences derived from penP gene flanked by the HpaII site and the AvaI The rest of the sequence in pOG2254, which includes the region from the AvaI site to the ClaI site, was derived from pBR322. Plasmid pOG2254 was linearized at the single AvaI site. The linearized DNA was treated with ExoIII enzyme for various lengths of time under the conditions specified by Guo, L. H., and Wu, R., *Nucleic Acids Research* 10:2065-2084, (1982). ExoIII enzyme converts the terminal regions of double-stranded DNA to single-stranded termini. Since the rate of ExoIII nuclease digestion can be controlled, samples were removed from the reaction mixture at different times and then pooled together. These DNA preparations were then treated with single-strand-specific nuclease S1 (obtained from Bethesda Research Laboratories, Inc. and used according to suppliers specifications). The S1 nuclease treatment specifically removes single-stranded DNA from the termini, thus generating flush-ended molecules.

DNA treated with ExoIII and S1 nucleases was then digested with EcoRI enzyme. The EcoRI site in the pOG2254 plasmid is located 5' to the penP promoter. Digestion with EcoRI releases a small fragment from these ExoIII and S1 treated DNA fragments, which contain the promoter of the penicillinase gene as well as various lengths of the amino terminal coding region of the penicillinase gene. These DNA fragments were fractionated on a gel. DNA fragments of approximately 300-400 base pairs were eluted from the gel and used for cloning experiments.

Each of these "short DNA fragments" has an EcoRI generated terminus on one side and a blunt-ended terminus on the other side. In order to clone these DNA fragments, plasmid pBR322 was digested with ClaI enzyme (position 23, which is located in the tetracycline-resistant gene promoter region, Sutcliffe, J. G., *Cold Spring Harbor Symposium Ouantitative Biology* 43:77-90 )1979)). The ClaI termini were then repaired with *Escherichia coli* DNA polymerase I Klenow fragment. This treated DNA was then digested with EcoRI which generated a large fragment containing an EcoRI generated terminus and a blunt-ended terminus. This large fragment from pBR322 was purified from gel and mixed with purified small fragment derived from penicillinase gene originated from pOG2254 as described above. The DNA's were ligated and then used to transform *Escherichia coli* competent cells CS412. Transformants resistant to tetracycline were selected on plates; the recombinant plasmids they harbor were characterized by digestion with EcoRI and HindIII enzymes which revealed that they have inserts derived from the penicillinase gene in the range of 300-400 base pairs as expected.

Figure 4:
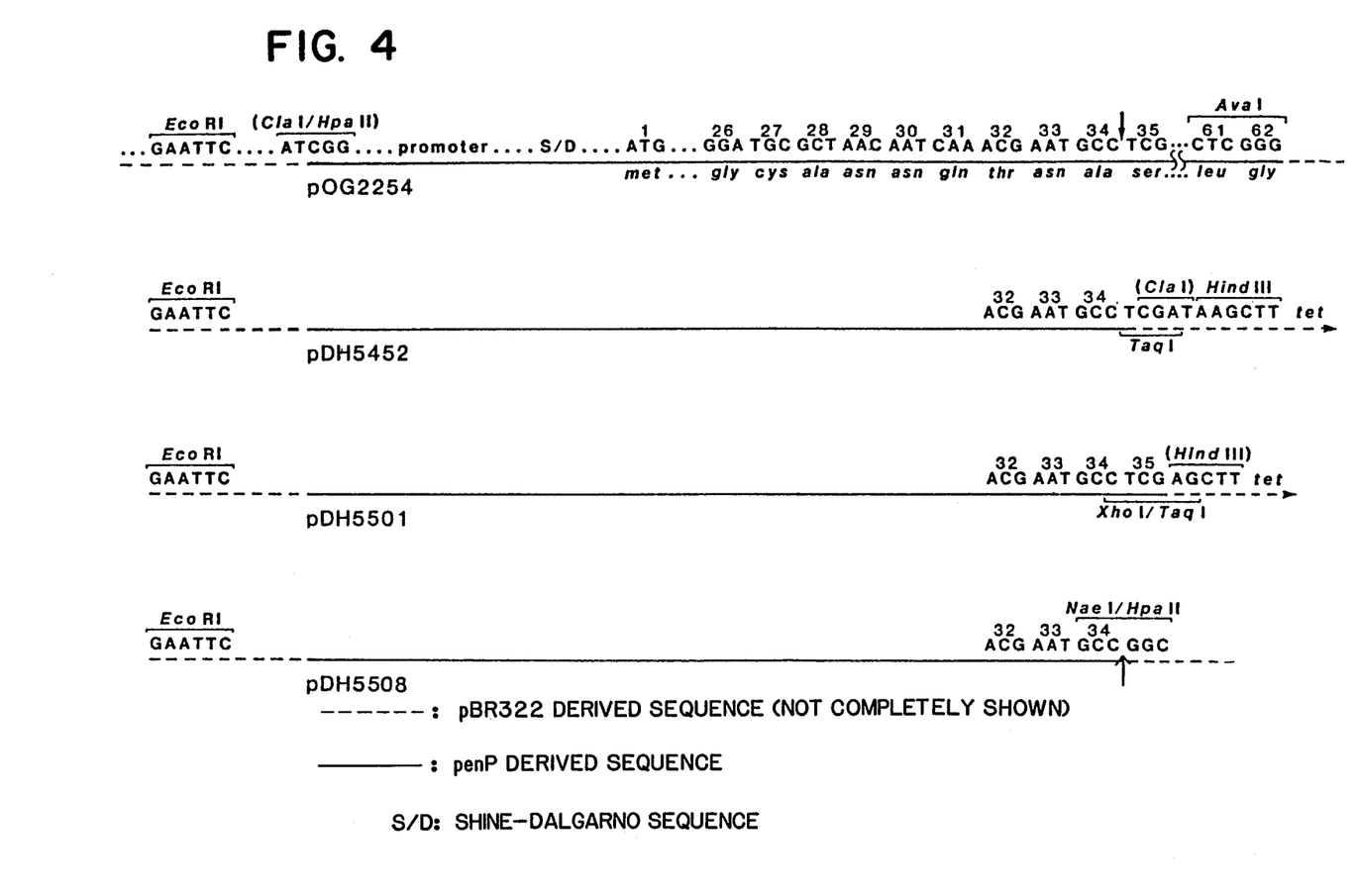
FIG. 4 is a nucleotide diagram illustrating a family of plasmids having convenient restriction enzyme sites flanking the penP promoter and signal sequence.

Several plasmid DNA's were prepared from different clones and the nucleotide sequences at the junction regions between penP and pBR322 sequences were analyzed using the Maxam and Gilbert method. Gilbert, W., and Maxam, H., in *Methods in Enzymology* 65:499-560 (Grossman, L., and Moldave, K. J., editors) Academic Press (1980). One of the plasmids designated pDH5452 had the sequence as shown in FIG. 4. Based on the DNA sequence, it appeared that the ExoIII and S1 nucleases generated deletions up to nucleotide T corresponding to the T in the coding sequence for the 35th amino acid of penP. This T was joined by ligation to the repaired ClaI site, originated from pBR322, having the sequence CGA. The junction sequence TCGA corresponds to the recognition sequence of restriction enzyme TaqI. Restriction digestion with TaqI enzyme generates CG protruding ends. Plasmid pDH5452 plasmid DNA was digested with TaqI enzyme and the 5' protruding-ends were filled in with DNA polymerase I Klenow fragment, using standard conditions, and then digested again with EcoRI enzyme. The fragment between EcoRI to repaired TaqI, which contains the promoter and the signal sequence of p, was purified from this preparation by elution from gel and cloned into pBR322. The vector pBR322 DNA had been digested with HindIII enzyme and then repaired with DNA polymerase under the conditions described above. Following digestion with RI, this vector fragment was ligated to the purified penP fragment from pDH5452 and transformed into *Escherichia coli* strain CS412. One transformant, phenotypically resistant to ampicillin and tetracycline was isolated. Plasmid DNA from this transformant was prepared and analyzed. It has the sequence shown in FIG. 4. This plasmid is designated pDH5501. The repaired TaqI site was ligated to the repaired III site and the new junction sequence, as shown in FIG. 4, has the following sequence: CTCGAG. Within this sequence, CTCG was derived from pDH5452 and the AG residues were derived from repaired HindIII site of pBR322. This hexanucleotide sequence CTCGAG is recognized by restriction enzyme XhoI and the central four nucleotide TCGA is recognized by restriction enzyme TaqI.

To further create additional restriction enzyme recognition sequences at the end of the penP signal sequence, plasmid pDH5508 was constructed. To generate this plasmid, plasmid DNA of pDH5501 was digested with NaeI enzyme which recognizes sequences in the region derived from pBR322 at four locations: 403, 770, 930, and 1284 (see Sutcliffe, J. G., *Cold Spring Harbor Symposium Quantitative Biology* 43:77-90 (1979)). I recognizes sequence GCCGGC. Digestion with the enzyme leaves a blunt-ended sequence GCC-3' and 5'-GGC. NaeI digested pDH5501 DNA was further digested with XhoI enzyme. This was then treated with single-strand-specific nuclease S1 which generates blunt-ended fragments at the XhoI site. This leaves the sequence GCC corresponding to nucleotide sequence for the 34th amino acids in the penP signal sequence. After ligation of the treated DNA (at 10 micrograms/ml concentration of DNA), it was used for transformation into competent *Escherichia coli* cells prepared from strain CS412. An ampicillin-resistant tetracycline-sensitive transformant was obtained which harbors a plasmid designated pDH5508. Restriction analysis of pDH5508 showed that it has two NaeI sites, the downstream (clock-wise from the EcoRI site) one corresponding to the NaeI site located originally in pBR322 at position 1284. The upstream I site corresponds to the junction sequence generated by S1 treated XhoI site which was ligated to the NaeI site originally located in pBR322 at position 930. The sequence located between the unique EcoRI site on pDH5508 and the first NaeI site downstream from it is the sequence derived from pDH5501 which contains penP promoter and the signal sequence of penicillinase. The NaeI site has the sequence GCCGGC, which can be cut both by NaeI enzyme and by HpaII enzymes.

Therefore, a series of plasmids was constructed, each of which has convenient restriction sites flanking the penP promoter and signal sequence. Plasmid pDH5452 has a TaqI restriction site, as well as a HindIII restriction site following the coding sequence of the signal peptide. Plasmid pDH5501 has an XhoI site and a TaqI site following the signal sequence, and plasmid pDH5508 has an NaeI site and a HpaII site following the signal sequence of penicillinase.

EXAMPLE V

Cloning of human growth hormone (hGH) cDNA and construction of plasmid pSYC709

Human pituitary glands were used as the source for the human growth hormone mRNA. The method used to isolate mRNA is the method described by Maniatis, T., Fritsch, E. F., and Sambrook, J., in Chapter 6 of *Molecular Cloning: A Laboratory Manual*, Cold Spring Harbor Laboratory (1982). The cDNA was made according to the published procedure and cloned into plasmid pBR322 (ATCC 37017) using the methods outlined in Chapter 7 of Maniatis, T., Fritsch, E. F., and Sambrook, J., *Molecular Cloning: A Laboratory Manual*, Cold Spring Harbor Laboratory (1982). The pBR322 plasmid DNA was then digested with PstI enzyme. Terminal transferase was then used in the presence of dGTP to tail this vector DNA. The GTP-tailed DNA was annealed to double-stranded cDNA which had been tailed with dCTP. The annealed DNA was used to transform bacteria *Escherichia coli* strain MM294. One tetracycline-resistant and ampicillin-sensitive transformant was identified (designated clone 20C4) which carries the hGH cDNA sequence in a plasmid (designated p20C4). The plasmid, p20C4, contains an hGH gene insert which can be digested with restriction enzymes BamHI and SmaI. These two enzymes generate a fragment of about 688 base pairs which is the same as the fragment published by Martial, J. A., Hallewell, R. A., Baxter, J. D., and Goodman, H. M., *Science* 205:602–607, (1979). Since internal restriction sites, e.g. PstI, PvuII, were found that also match sites published by Martial, J. A., Hallewell, R. A., Baxter, J. D., and Goodman, H. M., *Science* 205:602–607, (1979), it was concluded that clone 20C4 carries cDNA coding for human growth hormone.

Plasmids were isolated from clone 20C4. The plasmid DNA was digested with BamHI enzyme which cuts into the plasmid at two locations. One BamHI site cuts into the tetracycline (tet) gene in the pBR322 derived sequence and the other cuts into the cDNA sequence. The digested DNA was mixed with a synthetic oligoneuclotide having the following sequences: 5'-TTCCCAACCATT-3'. This 12-mer oligonucleotide sequence matches a coding sequence in the hGH sequence. It corresponds to the codons for the first four amino acids of the mature hGH protein sequence (Martial, J. A., Hallewell, R. A., Baxter, J. D., and Goodman, H. M., *Science* 205:602–607, (1979)), which are Phenylalanine-Proline-Threonine-Isoleucine (Phe-Pro-Thr-Ile). The 12-mer primer was mixed with BamHI-digested 20C4 plasmid DNA to convert the DNA sequence coding for human growth hormone into a more convenient structure for further manipulations.

The methods used for this conversion are described by Goeddel, D. V., Shepard, H. M., Yelverton, E., Leung, D., and Crea, R., *Nucleic Acids Research* 8:4057–4074 (1980). Essentially the primer was used to adapt the human growth hormone gene with a new sequence as Goeddel, D. V., Shepard, H. M., Yelverton, E., Leung, D., and Crea, R., *Nucleic Acids Research* 8:4057–4074 (1980), had done in adapting the interferon gene. The mixture containing primer and template DNA was denatured by heat and then treated with *Escherichia coli* DNA polymerase I Klenow fragment and dNTP, as described in Goeddel, D. V., Shepard, H. M., Yelverton, E., Leung, D., and Crea, R., *Nucleic Acids Research* 8:4057–4074 (1980). The DNA was then digested with SmaI enzyme. SmaI cuts hGH gene at the 3'-end of the gene (see Martial, J. A., Hallewell, R. A., Baxter, J. D., and Goodman, H. M., *Science* 205:602–607, (1979)). A fragment of roughly 572 base pairs was purified from gel. The fragment has the nucleotide sequence starting from the first codon for the phenylalanine (Phe) in the mature human growth hormone protein, and ending at the 3'-end shortly after the coding sequence of hGH gene (see Martial, J. A., Hallewell, R. A., Baxter, J. D., and Goodman, H. M., , *Science* 205:602–607 (1979)).

Figure 5:
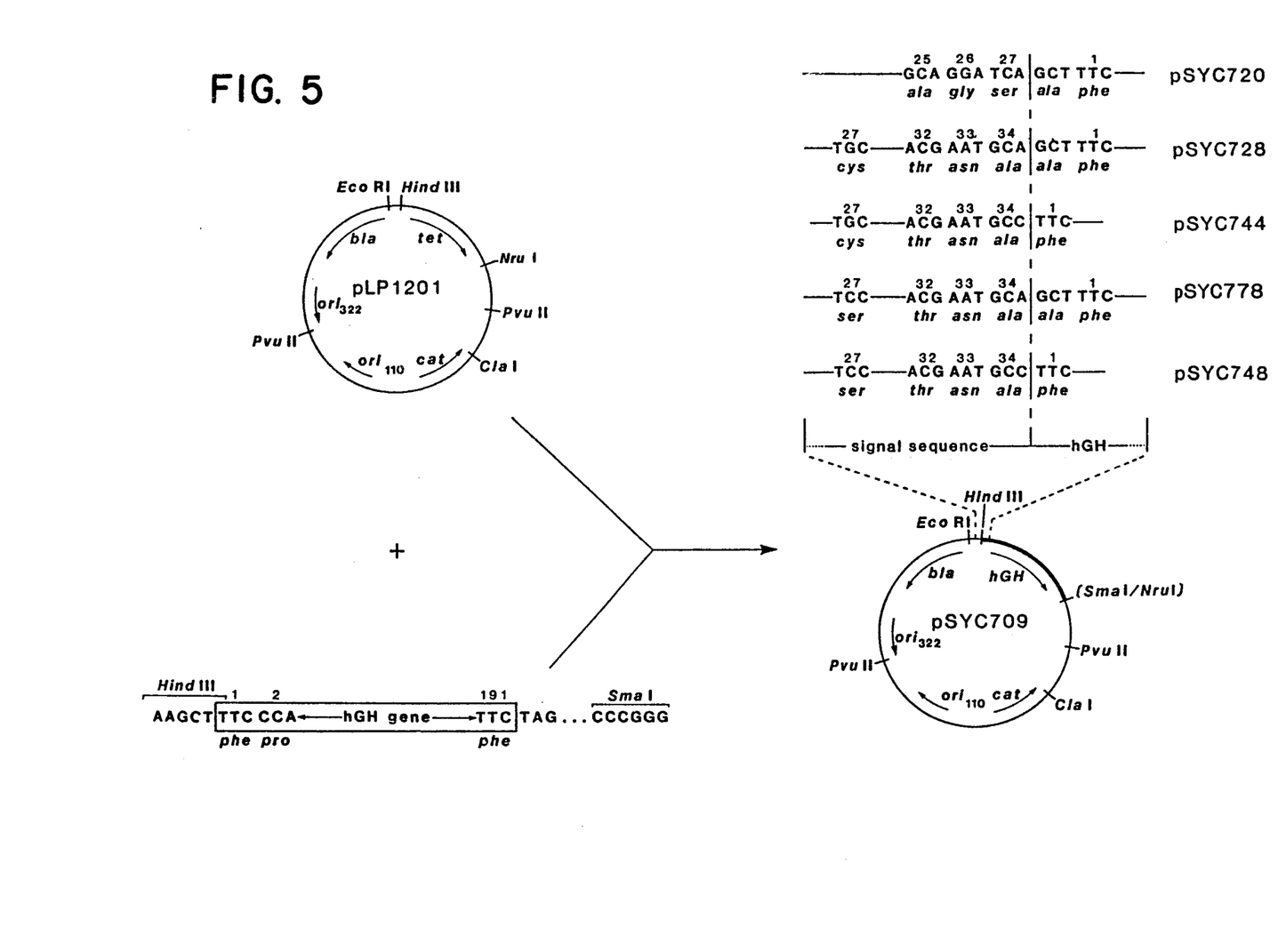
FIG. 5 is a diagram illustrating restriction enzyme maps of plasmids pLP1201 and pSYC709, in addition to nucleotide sequences in the area of penP-hGH fusions in pSYC709.

The vector DNA used to clone this fragment was pLP1201. Plasmid pLP1201 was derived from plasmid pDH5060 which in turn was derived as composite plasmid consisting of pBR322 (ATCC 37017) and the Bacillus plasmid pOG1196 (ATCC 31777). Plasmid pLP1201 is included in the general plasmid overview in FIG. 1. Essentially plasmid pDH5060 is the same as pLP1201 except that one of the HindIIII sites has been removed. Plasmid pLP1201 was digested with HindIIII enzyme and NruI enzyme, both of which cut the sequence derived from pBR322. This linearized DNA was further treated with DNA polymerase I Klenow fragment in the presence of four dNTP to generate blunt-ended fragments. The large fragment from treated pLP1201 DNA was purified on gel, and then ligated with the treated human growth hormone sequence as described above (using blunt-ended ligation conditions described by Maniatis, T., Fritsch, E. F., and Sambrook, J., *Molecular Cloning: A Laboratory Manual*, Cold Spring Harbor Laboratory (1982)). These fragments were joined together and then used for transformations into *Escherichia coli* strain CS412. Transformants which were phenotypically ampicillin-resistant and tetracycline-sensitive were further characterized by restriction analyses. One clone harboring a plasmid designated as pSYC709 is shown in FIG. 5. It has a unique III site as a result of the cloning which joined the hGH gene to the vector DNA. This plasmid also has a unique EcoRI site. Both the EcoRI and III sites can be cleaved and new fragments inserted which will be located upstream to the coding sequence of human growth hormone gene. This construction facilitates further expression work.

EXAMPLE VI

Use of an in vivo recombination method to construct plasmids containing fusion genes between penicillinase signal sequence and mature hGH gene Construction of plasmid pSYC709, which contains the coding sequence for mature hGH gene, is described in Example V. This plasmid replicates in both *Bacillus subtilis* and *Escherichia coli*. Two unique sites exist upstream from the hGH gene, i.e., an EcoRI site and a HindIII site. Plasmid pSYC709 was digested with III enzyme. Then, half the sample was treated with *Escherichia coli* DNA polymerase I Klenow fragment in the presence of four dNTP's to fill-in the ends; the other half of the preparation was digested with S1 nuclease to remove single strand protruding ends. Both preparations were then further digested with restriction enzyme EcoRI.

The large DNA fragments generated from these treatments were fractionated on a 0.8% agarose gel and purified after electrophoresis. The two preparations purified by these methodsd are: (A) the large fragment of pSYC709 which contains the EcoRI-generated end and a HindIII-generated end which has been filled in; (B) the large fragment of pSYC709 which contains an EcoRI-generated end and a S1 -treated HindIII-generated end.

In a separate experiment, DNA fragments which contain the penP promoter and the coding sequence for the signal peptide were prepared. Plasmid pDH5508, described in Example IV was digested in one experiment with I. In another experiment it was digested with HpaII and the HpaII digested preparation was treated with DNA polymerase I Klenow fragment in the presence of triphosphate nucleotide to generate blunt-ended fragments by the filling in reaction. These DNA preparations were then further digested with restriction enzyme EcoRI. The fragment which contains penicillinase promoter and signal sequence was purified from each of the two pDH5508 digests after fractionation on gels. The penP fragment generated by EcoRI and NaeI digestions was used to construct to plasmid pSYC744. The fragment generated by EcoRI enzyme and HpaII enzyme (followed by DNA polymerase I Klenow fragment reaction) was used for the constuction of plasmid pSYC728. This and other plasmids are outlined in the general overview presented in FIG. 1.

To construct plasmid pSYC728, the A fragment (the large fragment of pSYC709 prepared as described supra), and the EcoRI to HpaII penP fragment from pDH5508 were used. The fragments were ligated together and used for transformation into *Escherichia coli* competent CS412 cells. The EcoRI to NaeI penP fragment from pDH5508 and the B fragment (which was prepared from pSYC709 as described supra) were used in a similar fashion. These fragments were ligated and transformed into *Escherichia coli* CS412 cells. Transformants resistant to ampicillin were selected from these experiments and the DNA's analyzed after purification.

One clone generated from the first experiment was designated as plasmid pSYC728 and one plasmid from the second experiment was designated as pSYC744. They essentially have the structure as shown for plasmid pSYC709 in FIG. 5 except the region 5' to the hGH gene was altered. The original EcoRI to HindIII site region was replaced in both plasmids by a fragment which contains the sequence of penicillinase promoter and the signal peptide. For plasmid pSYC728 (as shown in FIG. 5), the sequence at the penP-hGH junction is GCAGCT. The GCA corresponds to the codon for the last (34th) amino acid in the signal peptide. The GCT, derived from the repaired HindIII site, codes for alanine (Ala). In plasmid pSYC728 the 34th amino acid is alanine which is followed a by phenlyalanine (Phe), coded for by the codon TTC. Since the sequence GCAGC in the hexanucleotide is recognized by Fnu4H1 restriction enzyme, plasmid pSYC728 DNA prepared from this clone was digested with Fnu4H1 enzyme. The presence of a site in this location was identified. This proved that it has the expected junction sequence as shown in FIG. 5.

For plasmid SYC744 a different method was used to prove that the sequence is correct. It has the expected sequence GAATGCCTTC at the penP-hGH junction, which corresponds to the coding sequence for the 32nd, 33rd, and 34th codons in the signal sequence and the first codon in the mature hGH protein. Since restriction enzyme I recognizes the GAANNNNTTC sequence, plasmid pSYC744 was digested with XmnI enzyme. The presence of the restriction site was found in the expected location. This substantiated the assigned sequence in pSYC744 as shown in FIG. 5. An analysis of the expression of these two plasmids is oulined in Example IX.

EXAMPLE VII

Figure 6:
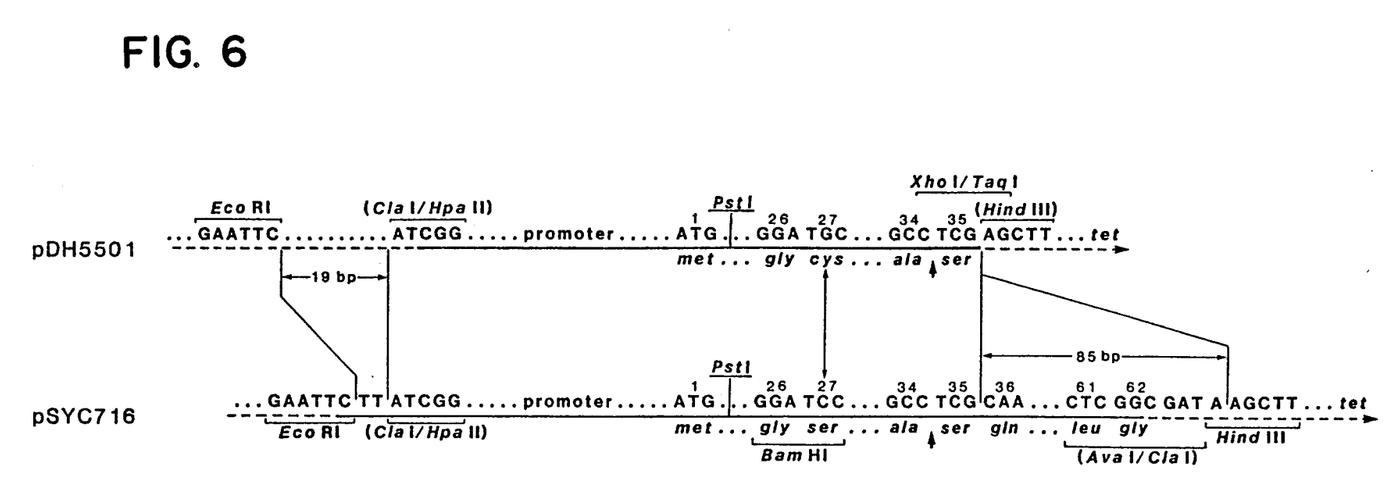
FIG. 6 is a codon diagram comparing the codon sequences of plasmid pDH5501 with the codon sequences of plasmid pSYC716.

Construction of plasmid pSYC720 which carries modified penP signal sequence and hGH genes Plasmid pSYC720 was constructed from a plasmid designated pSYC716. Plasmid pSYC716 was constructed by cloning a fragment containing modified penP signal sequence ($ser_{27}$ mutation), obtained from plasmid pSYC660, into plasmid pBR322. The pBR322 vector DNA was first digested with ClaI and EcoRI enzymes and this DNA was then repaired with DNA polymerase I Klenow polymerase fragment in the presence of four dNTP's to generate blunt-ends on the DNA fragments. In a separate experiment, plasmid pSYC660, which is identical to plasmid pSYC310-2, McLaughlin J. R., Chang, S.-Y., and Chang, S., *Nucleic Acid Research*, 10:3905-3919, (1982), except that the $Cys_{27}$ to $Ser_{27}$ mutation has been introduced into this plasmid, was digested with AluI enzyme and AvaI enzyme. AluI recognizes multiple sites in the plasmid, including the HindIII site as described in McLaughlin J. R., Chang, S.-Y., and Chang, S., *Nucleic Acid Research*, 10:3905-3919, (1982). I is located in the coding sequence corresponding to the codons for the 61st and 62nd amino acids in the penP gene (see Kroyer, J., and Chang, S., 15:343-347 (1981)). The digested DNA fragments were then repaired by DNA polymerase I Klenow fragment to generated blunt ends on all the fragments. The fragment containing penP promoter and the coding sequence for the first 62 amino acids was isolated after fractionation on gel. This purified fragment was used to ligate with pBR322 DNA which has been previously digested with EcoRI and ClaI enzymes and treated with DNA polymerase I as described supra. Upon transformation into *Escherichia coli* competent CS412 cells, an ampicillin-resistant tetracycline-resistant transformant was isolated from which a plasmid, designated as pSYC716, was identified. Plasmid pSYC716 has the structure shown in FIG. 6. It essentially contains most of the pBR322 sequence except that the region between the EcoRI site and the ClaIsite has been replaced the oenP sequence. The penP-derived sequence in pSYC716 is now flanked by the EcoRI site and the HindIII site in pSYC716.

Plasmid pSYC716 was digested with BamHI enzyme which cuts at a position corresponding to the codons for the 26th and the 27th amino acids of the signal peptide. The DNA ends were repaired with DNA polymerase I Klenow fragment and then digested again with EcorI enzyme. The fragment containing penP promoter and a portion of the signal sequence was purified. This was cloned into pSYC709, described in Example V, which had been previously digested with III enzyme. Following repair of the HindIII termini, the plasmid was digested with EcoRI. Ligation of the penP fragment derived from pSYC716 and the large EcoRI to HindIII fragment of pSYC709 was performed and the mixture used to transform *Escherichia coli* competent CS412 cells. One ampicillin-resistant transformant which harbors plasmid pSYC720 was further characterized. It carries the penP promoter and the first 27 amino acids of the modified signal peptide derived from the penP gene followed by Ala-Phe-Pro—sequence found in the growth hormone protein.

EXAMPLE VIII

Use of in vivo recombination to create fusion genes carrying the modified penP signal sequence and hGH sequences In order to introduce the cysteine$_{27}$-serine$_{27}$ mutation into the fusion genes, a method which involves the transformation of heteroduplex DNA made between a pair of parental plasmids to produce recombinants in vivo was utilized.

Figure 8:
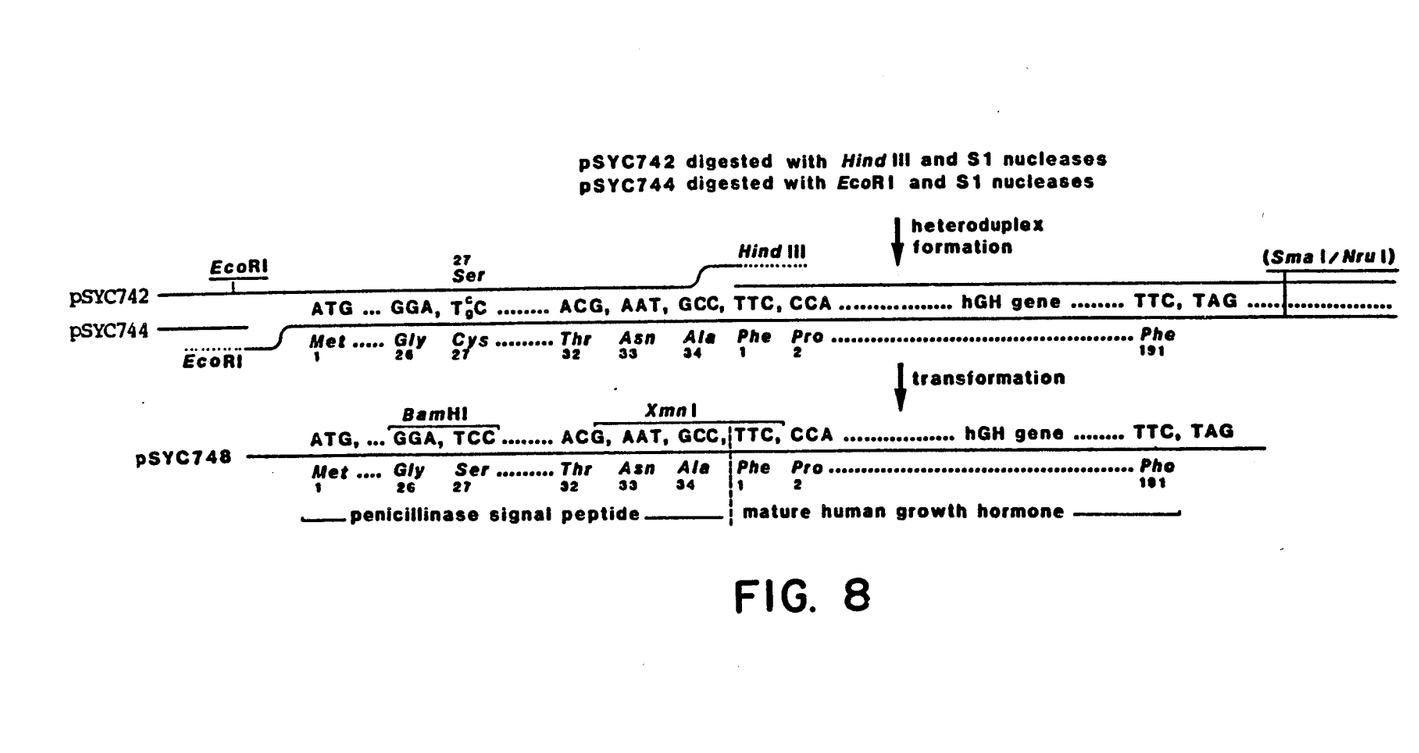
FIG. 8 is a codon diagram illustrating construction of pSYC748 by heteroduplex formation and in vivo recombination.

Construction of plasmids pSYC728 and pSYC744, which carry the fusion gene consisting of the wild-type signal sequence of penP and the protein sequence of hGH, are described in Example VI. Similar constructs have been prepared using the modified penP signal sequence which has the ser$_{27}$ mutation. These are plasmids pSYC778 and pSYC748; they are derived from plasmids pSYC728 and pSYC744, respectively. These plasmids are illustrated in FIG. 8. In constructing these plasmids, a method was used which allows in vivo genetic recombination in heteroduplexed plasmids. To achieve this, plasmid pSYC742 was made.

To construct plasmid pSYC742, plasmid pSYC716 was digested with EcoRI and HindIII enzymes. The small fragment, which contains penP promoter and the coding sequence for the first 62 amino acids was purified. Plasmid pSYC709 was digested with EcoRI and the HindIII enzymes and the digested DNA was ligated with the purified EcoRI to HindIII fragments derived from pSYC716. Upon ligation and transformation into competent CS412 cells, the purified plasmid DNA from one ampicillin-resistant transformant (designated the plasmid pSYC742) has the structure as expected. The short sequence located between the RI and III sites in pSYC742 is derived from pSYC716 and the large EcoRI to HindIII fragment is derived from pSYC709.

Parental plasmid pSYC742 was digested with HindIII enzyme to completion and the termini were treated with S1 nuclease.

In a separate experiment, the second parental plasmid, plasmid pSYC744, was digested with EcoRI enzyme and treated with S1 nuclease. These two digested and treated linearized DNA's were mixed with equal molar ratio (at a DNA concentration of 10 micrograms per ml) and heated by putting the test tube into a boiling water bath for 2 minutes and slowly cooled to allow homoduplexs and heteroduplexes to form. Homoduplexes have double-stranded duplex DNA wherein both strands are derived from the same parental plasmid, i.e. AA or A'A'. Heteroduplexes have double-stranded duplex DNA where each strand is derived from a separate parental plasmid, i.e. AA' or A'A. One form of the heteroduplex expected to form is shown in the FIG. 7. This figure shows only the portion of the heteroduplex containing the termini generated by EcoRI and HindIII enzymes. As shown in FIG. 7, the termini will form single-stranded hanging tails. Heteroduplex formed by this procedure were used to transform *Escherichai coli* competent CS412 cells. Ampicillin-resistant transformants were selected on plates and one of the transformants was characterized further. Plasmid DNA, now designated as pSYC748, was isolated and characterized further. Plasmid pSYC748 has a structure similar to that of plasmid pSYC744, the main difference is that pSYC748 has acquired a BamHI site indicating the presence of the Ser$_{27}$ mutation in this gene. The incorporation of the Ser$_{27}$ mutation is the result of transformation by heteroduplex DNA which has a mismatched base pair at the coding sequence corresponding to wild-type base pair at this location. Plasmid pSYC742 has a TCC codon for serine at this position, while plasmid pSYC744 has a TGC codon which codes for cysteine. Therefore after DNA repair in vivo, the mismatch was corrected according to the DNA sequence on either one of the two strands present in the plasmid. The one containing the Ser$_{27}$ mutation will be identified by the presence of a new BamHI site.

Using a similar procedure heteroduplex recombination was performed between plasmid pSYC742 and plasmid pSYC728. This generated plasmid pSYC778, which has a sequence similar to that of the pSYC728 except that pSYC778 has acquired the Ser$_{27}$ mutation. Therefore using this in vivo recombination procedure, two derivative recombination plasmids were successfully constructed, each of which carries a fusion gene comprised of the signal peptide of penP and the protein sequence of hGH. In plasmid pSYC778 the fusion gene has the 34 amino acids of the penP signal peptide (including the Ser$_{27}$ mutation) followed by alanine (ala) and phenylalanine (phe) and the rest of the hGH sequence. In plasmid pSYC748 the fusion gene has the 34 amino acids from the penP signal peptide, including the serine$_{27}$ mutation followed by the complete hGH sequence.

EXAMPLE IX

Analysis of various plasmids containing penP signal peptide fused to hGH gene

The plasmids containing the penP signal peptide sequences fused to the hGH hormone gene are bifunctional plasmids that can replicate in both *Bacillus subtilis* and *Escherichia coli*. Expression of hGh in *Bacillus sub-* tilis and *Escherichia coli* was measured by radioimmunoassay (RIA).

Five plasmids containing various gene fusions were analyzed. These five plasmids are detailed in the following table.

TABLE 1

| Coding Sequences | | Plasmids |
|---|---|---|
| 25 26 27     1<br>GCA GGA TCA    GCT TTC<br>ala gly ser       ala phe | | pSYC720 |
| 27    32   33   34     1<br>TGC...ACG AAT GCA   GCT TTC—<br>cys   thr   asn   ala      ala phe | | pSYC728 |
| 27    32   33   34     1<br>TGC...ACG AAT GCC   TTC—<br>cys   thr   asn   ala      phe | | pSYC744 |
| 27    32   33   34     1<br>TCC...ACG AAT GCA   GCT TTC—<br>ser   thr   asn   ala      ala phe | | pSYC778 |
| 27    32   33   34     1<br>TCC...ACG AAT GCC   TTC—<br>ser   thr   asn   ala      phe | | pSYC748 |
| —signal sequence————hGH— | | |
| HindIII | | |
| EcoRI | | |
| bla    hGH<br>pSYC709<br>See FIG. 5 for<br>further detail | | |

Each of the five plasmids was transformed into both *Escherichia coli* and *Bachillus subtilis* cells. More specifically, the plasmids were transformed into Bacillus Spo⁻ host strain SCR667 (Bacillus Genetic Stock Center strain 1S53, Bacillus Genetic Stock Center, Ohio State University). Chloramphenicol-resistant transformants were selected on plates and then grown in broth containing chloramphenicol at 5 micrograms/ml. For the *Bacillus subtilis* cultures, cells were grown in a 125 ml flask to OD (600 nanometers) equaling approximately 1.0 at 37° with vigorous shaking. The cells were then pelleted from the medium by centrifugation and the supernatant collected for use in the radioimmunoassay (RIA). For the RIA, a Cambridge Medical Diagnostics, Inc., RIA assay kit was used following the suppliers instructions. Kits and instructions are available from Cambridge Medical Diagnostics, Inc., Billerica, Maine. Use of the RIA made it possible to measure the level of hGH present in the culture fluid as a secreted exoprotein.

Under the conditions used, there was no evidence for cell lysis as revealed by protein patterns of gels.

*Escherichia coli* cells were grown and harvested as described for *Bacillus subtilia* with the exception that the *Escherichia coli* were further treated by the osmotic shock procedure originally developed by Nosel and Heppel, *Journal of Biological Chemistry* 241:3055–3062 (1966). This treatment was accomplished by pelleting and resuspending the growing cells ($OD_{600}$ approximately 1.0) in one tenth volume of buffer consisting of 50 mM tris, pH 7.4, 2.5 mM EDTA and 20% (weight/volume) sucrose. After ten minutes at 23° C., cells were pelleted by centrifugation and then resuspended with vortexing in an equal volume of cold (2° C.) deionized water. The solution was allowed to sit at 4° C. for 10 minutes. The cells were then pelleted by centrifugation. The supernatant fluid, which contains secreted periplasmic proteins was used for RIA.

The RIA results are shown in the following.

TABLE II

Secretion of hGH in *Bacillus subtilis* host SCR667 and *Escherichia coli* CS412 as measured by RIA

| | nanograms of hGH produced /$OD_{600}$ of cells | |
|---|---|---|
| Plasmid | *E. coli* periplasm | *B. subtilis* supernatant |
| pSYC709 | 0 | 0 |
| pSYC720 | 5890 | 53 |
| pSYC728 | 340 | 21 |
| pSYC778 | 2670 | 118 |
| pSYC744 | 640 | 26 |
| pSYC748 | 4350 | 66 |

From the results it can be seen that the presence of the serine$_{27}$ mutation in the signal sequence is providing significant improvement over the wild-type signal sequence thus allowing greater amounts of secrted protein to be expressed which is dissociated from membrane, i.e. expressed in the exoprotein form.

It may be seen therefore that the invention provides a method for producing modified signal peptide sequences derived from wild-type signal peptide sequences of the type that art capable of forming membrane-bound lipoproteins. According to the method of the invention, the modified signal peptide sequences are constructed by substituting the deoxyribonucleotide codon coding for the amino acid cysteine, found within the conserved region at the carboxy-terminal end or junction region of the signal peptide sequence, with a codon coding for an amino acid other than cysteine that will not function to form membrane-bound lipoprotein. Modified signal peptide sequences produced by the method of the invention will contain an amino acid S, i.e., an amino acid other than cysteine, in place of the cysteine contained within the conserved region located near the carboxy-terminal end or junction region of the signal peptide sequences. Modified signal peptide sequences of the present invention are useful in the creation of cloning vectors. The invention further provides a method for producing recombinant derivative plasmids in vivo.

Various modifications of the invention in addition to those shown and described herein will become apparent to those skilled in the art from the foregoing description and accompanying drawings. Such modifications are intended to fall within the scope of the appended claims.

What is claimed is:

1. A plasmid comprising a DNA sequence encoding a signal sequence comprising the sequence met lys leu trp phe ser thr leu lys leu lys lys ala ala ala val leu leu phe ser cys val ala leu ala gly ser ala asn asn gln thr asn ala.

2. The plasmid of claim 1 wherein the signal sequence from that of *B. licheniformis* penicillinase.

3. A plasmid comprising a DNA sequence encoding a signal sequence derived from *B. licheniformis* penicillinase wherein the cys$_{27}$ residue is altered to ser$_{27}$.

4. A microorganism transformed by the plasmid of claim 1.

5. A microorganism transformed by the plasmid of claim 2.

6. A microorganism transformed by the plasmid of claim 3.

* * * * *